(12) United States Patent
Averill et al.

(10) Patent No.: US 6,894,522 B2
(45) Date of Patent: May 17, 2005

(54) SPECIFIC SITE BACKSIDE UNDERLAYING AND MICROMASKING METHOD FOR ELECTRICAL CHARACTERIZATION OF SEMICONDUCTOR DEVICES

(75) Inventors: Barbara A. Averill, Newburgh, NY (US); Terence Kane, Wappingers Falls, NY (US); Darrell L. Miles, Wappingers Falls, NY (US); Richard W. Oldrey, Clintondale, NY (US); John D. Sylvestri, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 11 days.

(21) Appl. No.: 10/605,530

(22) Filed: Oct. 6, 2003

(65) Prior Publication Data

US 2005/0073333 A1 Apr. 7, 2005

(51) Int. Cl.$^7$ ............................................... G01R 31/26
(52) U.S. Cl. ......................... 324/765; 324/754; 257/48
(58) Field of Search ............................... 324/754–765, 324/158.1, 719; 257/48; 438/14–17

(56) References Cited

U.S. PATENT DOCUMENTS

| 5,698,474 | A | 12/1997 | Hurley | ...................... 437/249 |
|---|---|---|---|---|
| 5,786,236 | A | 7/1998 | Thompson et al. | ........... 438/60 |
| 5,990,562 | A | 11/1999 | Vallett | ........................ 257/774 |
| 6,078,057 | A | 6/2000 | Vallett | ........................ 257/48 |
| 6,242,931 | B1 | 6/2001 | Hembree et al. | ........... 324/754 |
| 6,245,587 | B1 | 6/2001 | Vallett | ........................ 438/18 |
| 6,255,124 | B1 | 7/2001 | Birdsley | ........................ 438/14 |
| 6,329,212 | B1 | 12/2001 | Dobrovolski | ................ 438/15 |
| 6,452,209 | B2 | 9/2002 | Vallett | ........................ 257/48 |

OTHER PUBLICATIONS

M. Mahanpour et al.; "Die and Solder Ball Defect Inspection in Flip Chipped Packaged Devices;" found at http://www-.fabtech.org/features/tap/articles/06.433.html, Total 9 Pages, Sep. 18, 2003.

*Primary Examiner*—Paresh Patel
(74) *Attorney, Agent, or Firm*—Lisa U. Jaklitsch; Cantor Colburn LLP

(57) ABSTRACT

A method for implementing backside probing of a semiconductor device includes isolating an identified defect area on a backside of the semiconductor device, and milling the identified defect area to an initial depth. Edges of the identified defect area are masked, wherein unmasked semiconductor material, beginning at the initial depth, is etched for a plurality of timed intervals until one or more active devices are reached. The one or more active devices are electrically probed.

15 Claims, 3 Drawing Sheets

US 6,894,522 B2

SPECIFIC SITE BACKSIDE UNDERLAYING AND MICROMASKING METHOD FOR ELECTRICAL CHARACTERIZATION OF SEMICONDUCTOR DEVICES

BACKGROUND OF INVENTION

The present invention relates generally to semiconductor device testing and, more particularly, to a method for specific site backside underlaying and micromasking for electrical characterization of semiconductor devices.

In the manufacture of semiconductor devices, the ability to obtain waveform measurements from internal nodes has been found to be critical to carrying out failure analysis and characterization. Often, active surfaces of the semiconductor devices are obscured by I/O (input/output) circuits, interconnect wiring, packaging, or limitations of the probing apparatus. During the integrated circuit development phase, early engineering hardware is typically characterized by subjecting the device to various test conditions such as speed, temperature, etc. Measuring and diagnosing the performance of these devices is done by acquiring waveforms from key circuit nodes within the device such as clock lines, enable signals, address buses, and data buses. If the early engineering hardware does not perform adequately, or is non-functional, it is critical to be able to trace back signals to the source of the problem. A convenient mode of detecting such failure source is by waveform analysis. The ability to diagnose problems by waveform analysis is also necessary during manufacture and throughout the life of the product so that corrective action can be taken.

Those skilled in the art will recognize that waveforms can be acquired from internal circuit nodes by direct-contact mechanical probing or electron beam probing. Additional techniques, such as laser-induced light, have also been reported. In order to prepare a device for diagnosis, it is necessary to establish electrical contact with a tester and one or more of the numerous I/O circuits in the device. In some instances, these I/O circuits are placed in the periphery of the device, or located in a manner to provide some degree of access to the device's active surface by some form of mechanical or electron beam probe during operation. However, as a result of increasing circuit complexity, a trend toward higher density packaging, or the density of the I/O circuits and related probes needed to activate the device, improvements in semiconductor device access for mechanical or electron beam probe are needed.

To facilitate electrical access to the I/O of the IC, additional circuits and pads are frequently positioned adjacent to, or on the uppermost level of the IC die. Quite frequently, such IC dies with I/O circuit elements situated on the top surface have the disadvantage of obstructing internal circuitry. Additionally, packaging methods, often referred to as a "flip-chip", "C4", or direct chip attach (DCA), can be attached upside-down, or flipped onto a package substrate, or directly onto a circuit board, flexible cable, or other assembly into which the IC is interconnected. As a result, the internal circuit nodes of the IC are buried and inaccessible for characterizing electrical circuit performance, performing diagnostic testing, or performing failure analysis while the IC is operating normally and in a fully functioning state.

In particular, with the emergence of technologies such as embedded dynamic random access memory (eDRAM), system on a chip (SOC), and silicon on insulator (SOI) devices, for example, effective backside electrical characterization techniques are desired given the multiple wiring levels of such devices.

SUMMARY OF INVENTION

The foregoing discussed drawbacks and deficiencies of the prior art are overcome or alleviated by a method for implementing backside probing of a semiconductor device. In an exemplary embodiment, the method includes isolating an identified defect area on a backside of the semiconductor device, and milling the identified defect area to an initial depth. Edges of the identified defect area are masked, wherein unmasked semiconductor material, beginning at the initial depth, is etched for a plurality of timed intervals until one or more active devices are reached. The one or more active devices are electrically probed.

In another aspect, a method for implementing backside probing of a semiconductor device includes isolating an identified defect area on a backside of the semiconductor device, and milling the identified defect area to an initial depth. Edges of the identified defect area are masked, wherein unmasked semiconductor material, beginning at the initial depth, is etched for a plurality of timed intervals until one or more active devices are reached. The one or more active devices are electrically probed, and a resulting cavity produced from the milling and etching of backside of the semiconductor device is backfilled. The semiconductor device is cross-sectioned to locate one or more fail mechanisms associated therewith.

BRIEF DESCRIPTION OF DRAWINGS

Referring to the exemplary drawings wherein like elements are numbered alike in the several figures.

DETAILED DESCRIPTION

Disclosed herein is a method of backside thinning of a semiconductor device in a non-destructive manner so as to allow desired tests and/or other physical analyses to be performed. Briefly stated, the method implements an initial milling step to about 75±15 microns in thickness with respect to the circuit side of a semiconductor substrate. After the initial milling, a sequence of masking and etching steps are used to reach the active devices of the substrate. The masking operates to protect those features (such as corners and edges) that etch at a faster rate, thereby preserving planar uniformity of the originally created cavity from the milling. Once the active devices are reached, they may be probed/tested by appropriate means, and the cavity is thereafter backfilled.

Figure 1:
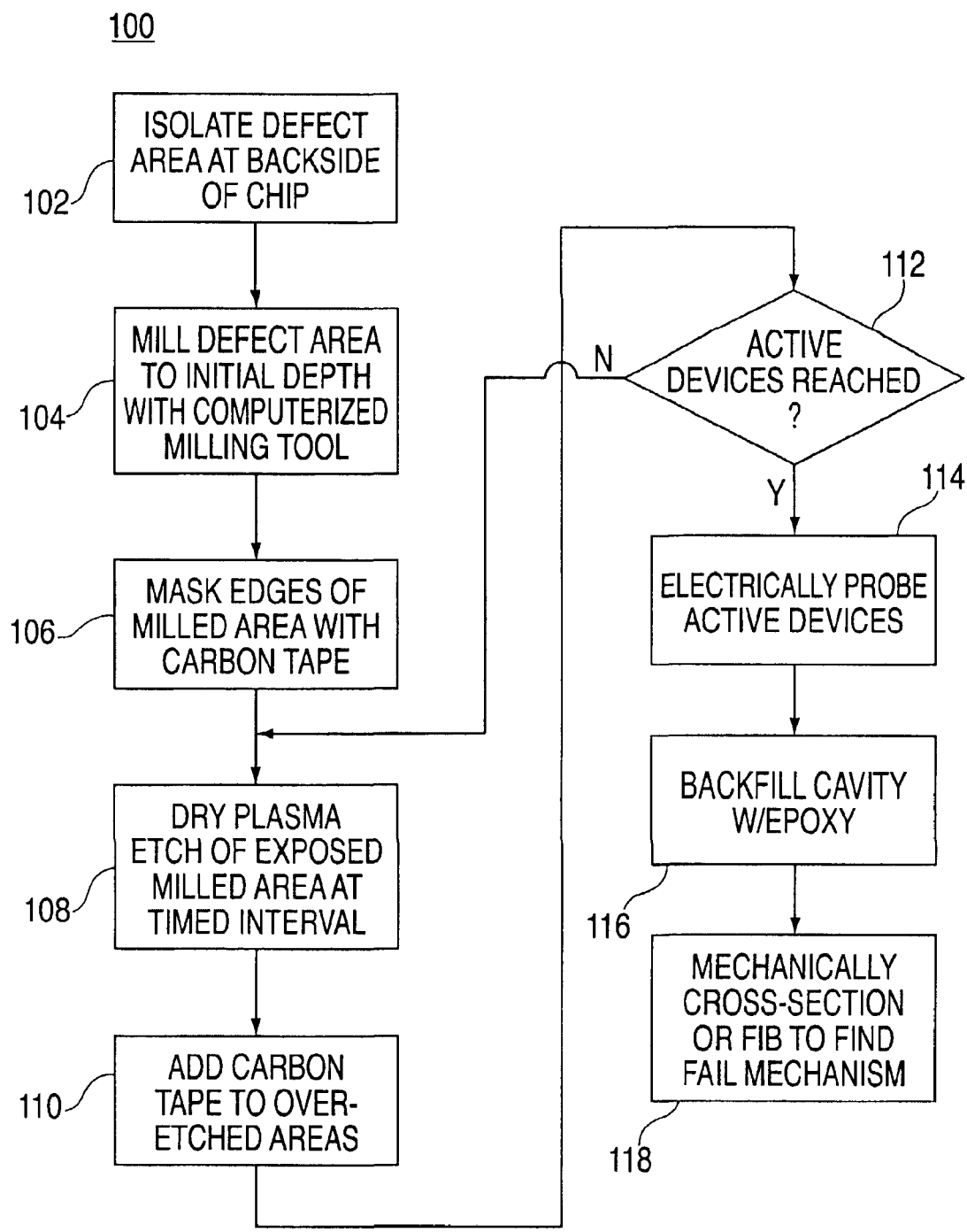
FIG. 1 is a process flow diagram illustrating a method 100 for implementing backside probing of a semiconductor device, in accordance with an embodiment of the invention.

FIG. 1 is a process flow diagram illustrating a method 100 for implementing backside probing of a semiconductor device, in accordance with an embodiment of the invention. The method 100 may be applied to any of a number of different types of semiconductor devices including, but not limited to, dynamic random access memory (DRAM), embedded DRAM (eDRAM), system on a chip (SOC), and silicon on insulator (SOI) devices, for example. As shown in block 102, the method 100 begins by isolating a defect area at the backside of the semiconductor chip (die), the dimensions of which may be furnished by the chip customer. Then, at block 104, the area of concern is initially milled (i.e., thinned) by a computerized backside-thinning process to a desired final thickness. (e.g., 75±15 microns).

A suitable example of a backside-thinning tool that may be used for this purpose is the Chip UnZip™ System, available from Hypervision, Inc. As described in U.S. Pat. No. 5,698,474 to Hurley (the contents of which are incorporated herein by reference), the technique utilizes computer numerically controlled (CNC) milling equipment for high z-axis precision, and further produces rectangular or square cuts with minimally radiused edges. Thus, rather than thinning an entire wafer, selected die on the wafer may be thinned without risk of wafer fracture. Moreover, the step of milling the backside of a die to an initial thickness through a computer controlled process results in a more uniform and planar surface than would be achieved by etching the entire bulk area of the substrate.

Once the initial thickness of bulk silicon is milled, a series of dry plasma etches are implemented for specifically timed durations in order to reach active device areas, such as deep trenches in an eDRAM device, for example. As shown at block 106, the edges of the milled area of the die are covered with an electrically conductive, black carbon tape to mask the edges from the plasma etch. Then, at block 108, an initial dry plasma etch interval is carried out to etch the exposed portions of the milled die. In one embodiment, the etch intervals are implemented using sulfur hexafluoride ($SF_6$) gas at a flow rate of about 60 to about 100 standard cubic centimeters (SCCM) per minute, for a duration of about 2 to about 3 minutes. Following a given etch interval, any over-etched areas may be covered with additional black carbon tape, as shown at block 110. The additional masking tape may be applied, for example, by placing strips diagonally over the corners created by the etching process within the milled area.

Decision block 112 determines whether the latest etching step has reached the active devices to be probed. If not, the method 100 returns to block 108 for further etch intervals, wherein after each interval, any exposed areas are covered with the black carbon tape. It is also contemplated that the tape could be removed if portions thereof are masking any under-etched areas, as well. Once the active devices (e.g., DRAM storage capacitors) are reached, they may be individually probed in order to identify an individual failure(s), as shown in block 114. Finally, the resulting cavity may be backfilled with an epoxy or other suitable material, as shown in block 116, and the sample may be further mechanically cross-sectioned, or a focused ion beam (FIB) applied in order to find the specific fail mechanism as shown in block 118.

Figure 2:
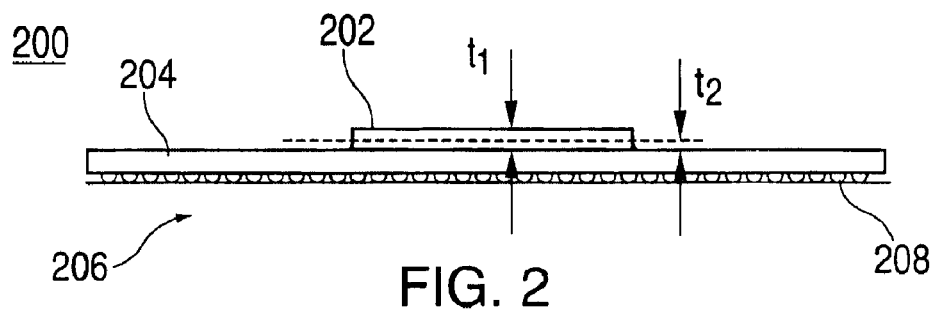
FIG. 2 is a cross-sectional view of an integrated circuit die mounted face down on a circuit board, prior to the initial milling thereof.

FIGS. 2 through 6 illustrate exemplary views of an integrated circuit (IC) package 200 suitable for use in conjunction with the above described backside probing method 100. Although the package type depicted in the figures is a flip-chip, C4 bonded organic substrate, it will be appreciated this is not the only type package on which the milling/etching/probing may be used. As is particularly shown in FIG. 2, the package 200 features an IC die 202 attached to a package body 204, which is in turn bonded to substrate 206 through C4 solder balls 208. In accordance with flip-chip packaging, the backside of the die 202 is arranged in an upward orientation. Prior to the computerized milling, the die 202 has an initial thickness, $t_1$. The horizontal dashed line shown in FIG. 2 is illustrative of the remaining thickness, $t_2$, of the die 202 following the computerized milling step, as described above. For purposes of illustration, the entire surface of the die 202 is shown milled in the figures. However, it should be understood that the computerized milling process may be used to mill a selected portion of the backside of the die 202.

Figure 3:
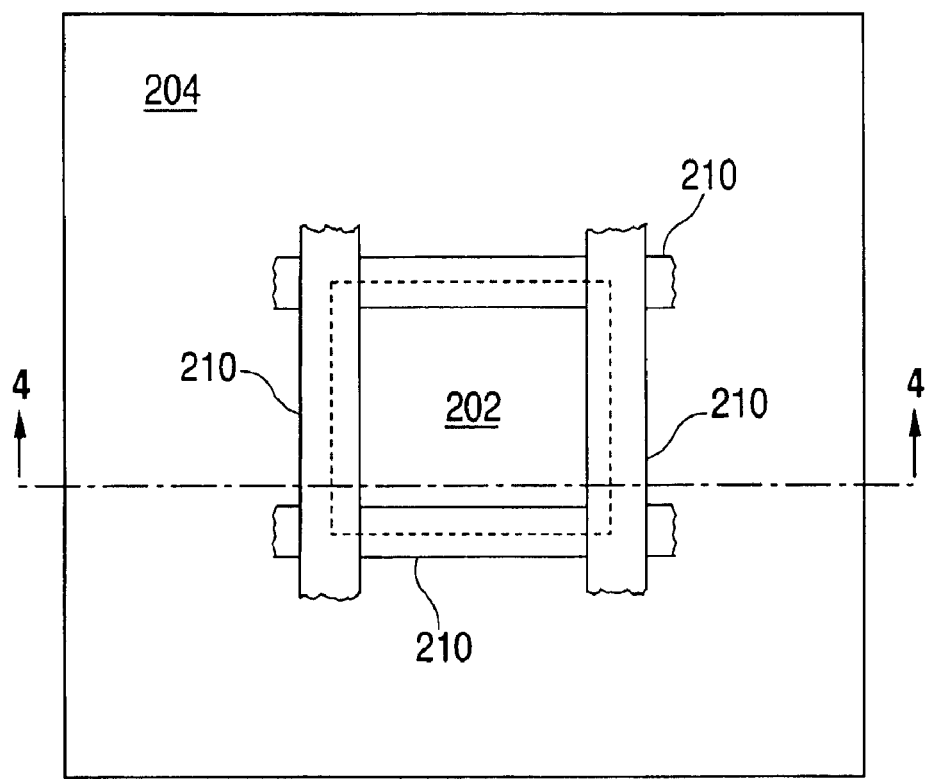
FIG. 3 is a top down view of the integrated circuit die following the milling process, particularly illustrating the use of masking tape during the etching process and in accordance with the method of FIG. 1.

FIG. 3 is a top down view of the integrated circuit die 202 following the milling process. Once the die 202 is milled to the desired initial depth (i.e., thickness $t_2$), pieces of black carbon tape 210 are used to cover the outer edges of the die 202. This allows for the quick and selectively masking of the area(s) of concern. Moreover, the tape 210 can be adjusted in between successive etch intervals in the plasma tool to cover up and/or expose more die as needed. While in the exemplary embodiment an electrically conductive, double backed carbon tape is used, other types of suitable etching mask tapes are also contemplated.

Figure 4:
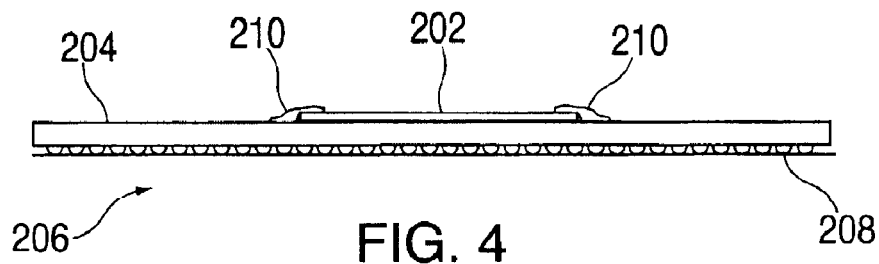
FIG. 4 is a cross-sectional view of the integrated circuit die, taken along the lines 4—4 of FIG. 3.
Figure 5:
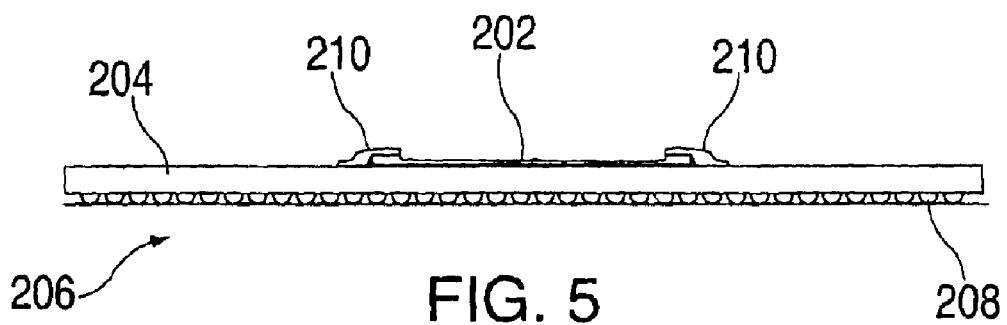
FIG. 5 is a cross-sectional view of the integrated circuit die of FIG. 4, following an etching interval of the exposed portion of the die.

FIG. 4 is a cross-sectional view of the integrated circuit die 202, taken along the lines 4—4 of FIG. 3. Again, the masking tape 210 is initially applied over the edges of the die 202 prior to the initial etching interval, such that only the exposed center of the die 202 is subjected to the plasma etching. FIG. 5 illustrates the masked die 202, following one or more of the etching intervals. The masked outer edges of the die 202 remain at the initially milled thickness, $t_2$, while the exposed area in the center of the die 202 has been thinned in order to approach the active devices therein.

Figure 6:
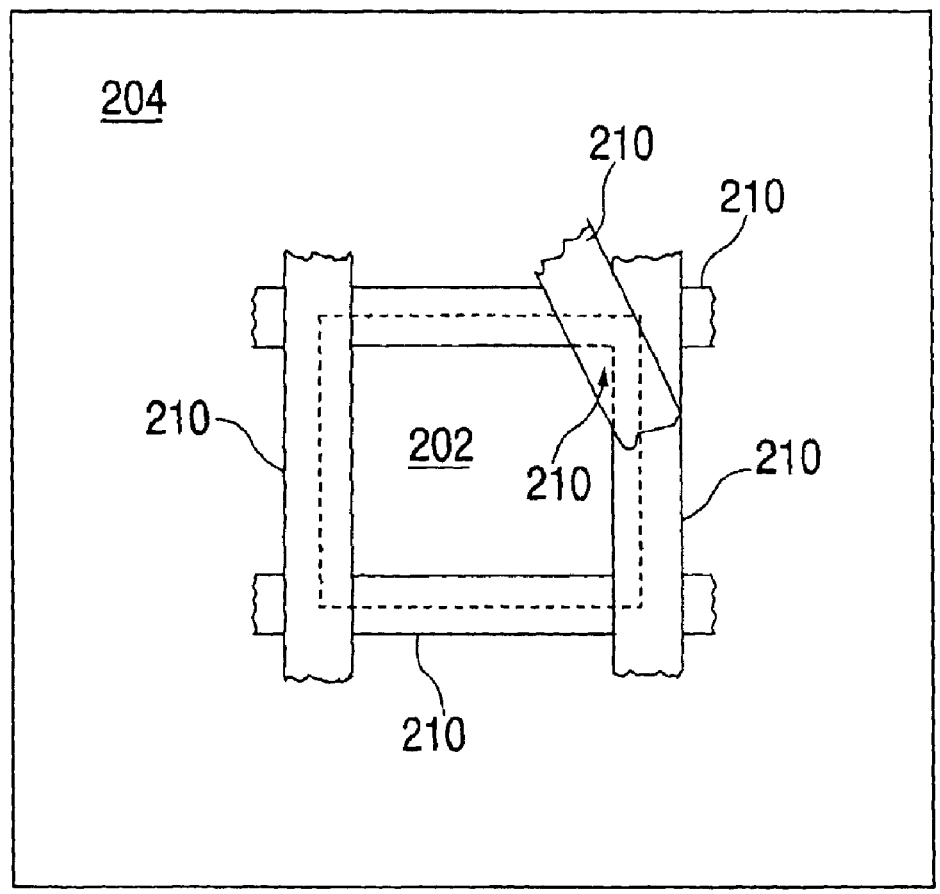
FIG. 6 is another top down view of the integrated circuit die, illustrating the use of additional masking to cover up over-etched portions of the die.

As discussed earlier, while the etching process progresses, the tape 210 may be removed, added or otherwise adjusted to cover areas that are etching at a faster rate than desired. For example, if it is determined after a particular etch interval that the upper right hand corner area of exposed die 202 (as shown in FIG. 3) has etched too quickly, then this area may be protected by additional masking during the next etch interval. This is illustrated in FIG. 6, in which an additional piece of tape 210 is placed over the upper right corner of exposed die 202 so as to protect an over-etched region 212. Accordingly, if during the subsequent etch interval, the overall etched thickness of die 202 has returned to an acceptable level of uniformity, then the extra piece of tape 210 could be removed for the following etch interval.

While the invention has been described with reference to a preferred embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for implementing backside probing of a semiconductor device, the method comprising:

isolating an identified defect area on a backside of the semiconductor device;

milling said identified defect area to an initial depth;

masking edges of said identified defect area;

etching unmasked semiconductor material within the semiconductor device, beginning at said initial depth, for a plurality of timed intervals until one or more active devices are reached; and electrically probing said one or more active devices.

2. The method of claim 1, further comprising backfilling a resulting cavity produced from said milling and said etching said backside of the semiconductor device.

3. The method of claim 1, further comprising masking over-etched areas of said backside of the semiconductor device following one or more of said timed etching intervals.

4. The method of claim 1, wherein said milling to an initial depth is implemented with a computerized milling tool.

5. The method of claim 4, wherein said initial depth results in a final thickness of about 60 to about 90 microns.

6. The method of claim 1, wherein said etching further comprises a dry plasma etch utilizing sulfur hexafluoride ($SF_6$) at a flow rate of about 60 to about 100 standard cubic centimeters (SCCM) per minute, for a duration of about 2 to about 3 minutes.

7. The method of claim 2, wherein said resulting cavity is backfilled with epoxy.

8. The method of claim 3, wherein said masking said over-etched areas of said backside of the semiconductor device is implemented by covering exposed areas with carbon tape.

9. A method for implementing backside probing of a semiconductor die, the method comprising:

isolating an identified defect area on a backside of the semiconductor die;

milling said identified defect area to an initial depth;

masking edges of said identified defect area;

etching unmasked semiconductor material, beginning at said initial depth, for a plurality of timed intervals until one or more active devices are reached;

electrically probing said one or more active devices;

backfilling a resulting cavity produced from said milling and said etching said backside of the semiconductor device; and cross sectioning the semiconductor device to locate one or more fail mechanisms associated therewith.

10. The method of claim 9, further comprising masking over-etched areas of said backside of the semiconductor device following one or more of said timed etching intervals.

11. The method of claim 9, wherein said milling to an initial depth is implemented with a computerized milling tool.

12. The method of claim 11, wherein said initial depth results in a final thickness of about 60 to about 90 microns.

13. The method of claim 9, wherein said etching further comprises a dry plasma etch utilizing sulfur hexafluoride ($SF_6$) at a flow rate of about 60 to about 100 standard cubic centimeters (SCCM) per minute, for a duration of about 2 to about 3 minutes.

14. The method of claim 9, wherein said resulting cavity is backfilled with epoxy.

15. The method of claim 10, wherein said masking said over-etched areas of said backside of the semiconductor device is implemented by covering exposed areas with carbon tape.

* * * * *